US00PP09239P

United States Patent [19]

McGredy

[11] Patent Number: Plant 9,239

[45] Date of Patent: Aug. 15, 1995

[54] HYBRID TEA ROSE PLANT NAMED 'MACSPEEGO'

[75] Inventor: Sam McGredy, Auckland, New Zealand

[73] Assignee: DeVor Nurseries, Inc., Watsonville, Calif.

[21] Appl. No.: 215,291

[22] Filed: Mar. 18, 1994

[51] Int. Cl.[6] ..... A01H 5/00

[52] U.S. Cl. ..... Plt./12

[58] Field of Search ..... Plt. 11, 12, 13, 22, Plt. 20

*Primary Examiner*—Howard J. Locker

*Attorney, Agent, or Firm*—Christie, Parker & Hale

[57] ABSTRACT

A new Hybrid Tea rose plant producing red bicolor flowers.

1 Drawing Sheet

SUMMARY OF THE INVENTION

The present invention relates to a new and distinct variety of rose plant of the Hybrid Tea rose class which was originated by crossing as seed parent the variety known as 'Howard Morrison' and as pollen parent the variety known as 'Esmeralda'. The varietal denomination of this new rose is 'Macspeego'.

Among the novel characteristics possessed by this new variety which distinguish it from its parents and all other varieties of which I am aware are its attractive red bicolor flowers.

Asexual reproduction by budding of the new variety as performed in Watsonville, Calif., shows that the foregoing and other distinguishing characteristics come true to form and are established and transmitted through succeeding propagations.

COMPARISON WITH PARENTS

Flowers of 'Howard Morrison' are straight scarlet whereas the new variety flowers are a unique red bicolor and much bigger. 'Esmeralda' flowers are pink bicolor and 'Macspeego' is a red bicolor.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Howard Morrison'.

*Pollen parent.*—'Esmeralda'.

Class: Hybrid Tea.

The following is a detailed description of my new variety, of new specimens grown outdoors in New Plymouth, New Zealand in the month of January. The color terminology used is in accordance with the Royal Horticultural Society Colour Chart (RHSCC), and refers to plate numbers in the aforementioned color chart. Phenotypic expression may vary depending on light, environmental and cultural conditions.

FLOWER

Blooming habit: Recurrent.

A. Bud:

(1) *Size.*—Medium, about 4 cm wide by 6 cm long.

(2) *Form.*—Ovoid.

(3) *Color.*—When sepals first divide, near 46A heavily washed with near 53A; after petals begin to unfurl, near 45A washed with near 53B; inside reverse near 46B washed with near 48D.

(4) *Sepals.*—Very pointed, acuminate, longer than bud, overall sepal length about 4–5 cm.

(5) *Peduncle.*—Length: About 10 cm. Aspect: Straight, very fine prickles. Strength: Moderately erect. Color: Near 146D.

(6) *Bracts.*—None observed.

B. Bloom:

(1) *Size.*—Average size when fully expanded — about 12 cm.

(2) *Borne.*—Normally singly, one to a stem but sometimes several together in sprays of 5 to 6 blooms.

(3) *Form.*—Imbricated, loosely rolled outward, only slightly ruffled at maturity.

(4) *Petalage.*—Number of petals under normal conditions — about 30–36.

(5) *Color.*—$\frac{1}{3}$ to $\frac{1}{2}$ open: top surface of outer petals is near 46B; undersurface of outer petals is near 54D; top surface of inner petals is near 46B; undersurface of inner petals is near 54D; color at base of petals (point of attachment) is near 160B and the general tonality from a distance is a distinct bicolor red and washed light pink. Fully open blooms: top surface of outer petals is near 46B; undersurface of outer petals is near 46B washed with near 49C; top surface of inner petals is near 45A; undersurface of inner petals is near 49C with the edges washed with near 45A; color at base of petals (point of attachment) is near 160B and the general tonality from a distance is reddish pink, bicolor effect somewhat diminished. General tonality of open bloom is vibrant red.

C. Petals:

(1) *Texture.*—Thick, firm.

(2) *Appearance.*—Inside velvety and outside matte.

(3) *Form.*—Slightly lobed, heart-shaped.

(4) *Arrangement.*—Regularly arranged, imbricated.

(5) *Petaloids.*—Very few, becoming clear of reproductive organs.

(6) *Fragrance.*—Very slight, sweet.

(7) *Lasting quality.*—Long-lasting on plant, about 10–12 days; lasts as cut bloom about 5–7 days.

(8) *Persistence.*—Drop off cleanly.

REPRODUCTIVE ORGANS

A. Stamens:
(1) *Arrangement.*—Regularly arranged around styles.
(2) *Anthers.*—Color near 20B.
(3) *Filaments.*—Near 46C.
(4) *Pollen.*—Color near 20C.

B. Pistils:
(1) *Styles.*—Uneven length, about 6–8 mm.
(2) *Stigmas.*—Color near 162C.

C. Characteristics of hips: Urn-shaped, few, about 3 cm, bright orange-scarlet, seeds protrude.

PLANT

A. Form: Upright, bushy.
B. Growth: Vigorous, about 92 cm in first season.
C. Foliage: Compound 3 and 5 leaflets.
(1) *Size.*—Large.
(2) *Quantity.*—Abundant.
(3) *Color.*—New foliage — upper side near 146B overlaid with near 176A; underside near 146B overlaid with near 176B; old foliage — upper side near 147A, underside near 147C.
(4) *Shape.*—Ovoid.
(5) *Texture.*—Shiny, smooth; underside matte.
(6) *Edge.*—Serrate.

(7) *Serration.*—Dentate.
(8) *Leaf stem.*—Color — medium green.
(9) *Stipules.*—Medium length.
(10) *Rachis.*—Few prickles.
(11) *Auricle.*—Long.
(12) *Resistance to disease.*—Blackspot — moderate; mildew — very good; rust — very good.

D. Wood:
(1) *New wood.*—Near 146C.
(2) *Old wood.*—Near 146C, smooth.

E. Flower stem: About 75 cm from last cut.

F. Thorns:
*Quantity.*—On main stalk, ordinary; on laterals from stalk, ordinary.
*Form.*—Thin, slightly curved downward, acuminate.
*Length.*—Medium.
*Color.*—Near 178B when young.
*Position.*—Regular.
*Prickles.*—There are no prickles, only thorns.

F. Winter hardiness: Winter-hardy in New Plymouth, New Zealand and in Watsonville, Calif.

I claim:

1. A new and distinct variety of rose plant of the Hybrid Tea rose class, substantially as shown and described.

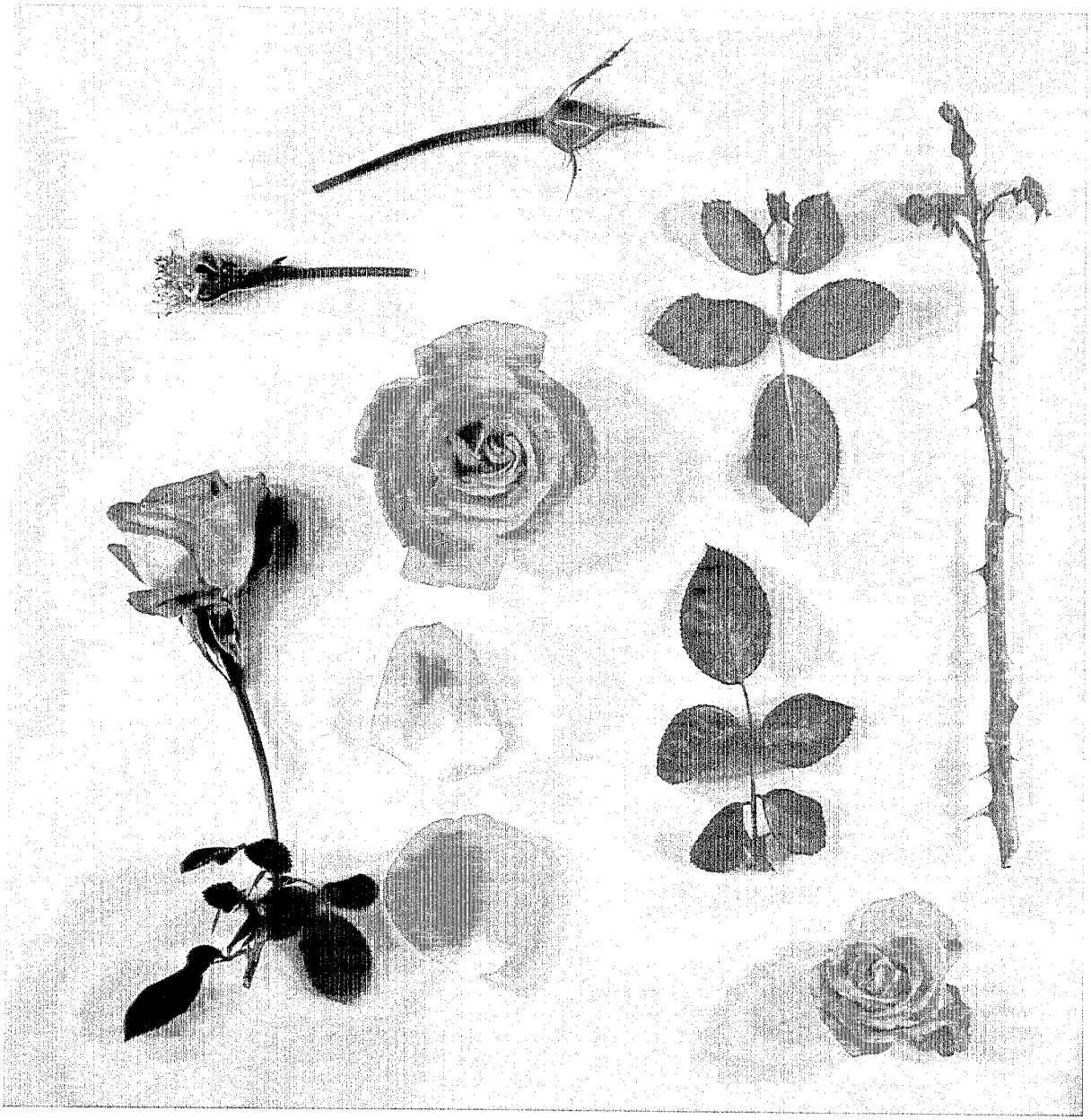

* * * * *